(12) United States Patent
Chen et al.

(10) Patent No.: US 7,892,540 B2
(45) Date of Patent: Feb. 22, 2011

(54) B7-H1 AND METHODS OF DIAGNOSIS, PROGNOSIS, AND TREATMENT OF CANCER

(75) Inventors: Lieping Chen, Sparks Glencoe, MD (US); Scott E. Strome, Rochester, MN (US); Eugene D. Kwon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 124 days.

(21) Appl. No.: 11/245,713

(22) Filed: Oct. 6, 2005

(65) Prior Publication Data

US 2006/0083744 A1 Apr. 20, 2006

Related U.S. Application Data

(60) Provisional application No. 60/616,590, filed on Oct. 6, 2004, provisional application No. 60/642,794, filed on Jan. 11, 2005.

(51) Int. Cl.
*A61K 39/395* (2006.01)
(52) U.S. Cl. .................................... 424/130.1; 435/7.1
(58) Field of Classification Search .............. 424/130.1; 435/7.1
See application file for complete search history.

(56) References Cited

U.S. PATENT DOCUMENTS

| | | | |
|---|---|---|---|
| 7,101,550 B2* | 9/2006 | Wood et al. .............. | 424/144.1 |
| 2002/0102651 A1 | 8/2002 | Freeman et al. | |
| 2003/0039653 A1 | 2/2003 | Chen et al. | |
| 2003/0044768 A1 | 3/2003 | Wood et al. | |
| 2006/0110383 A1 | 5/2006 | Honjo et al. | |
| 2006/0153841 A1 | 7/2006 | Freeman et al. | |

FOREIGN PATENT DOCUMENTS

| | | |
|---|---|---|
| WO | WO01/14556 | 3/2001 |
| WO | WO 02/00730 | 1/2002 |
| WO | WO 2004/004771 | 1/2004 |
| WO | WO 2004/077060 | 10/2004 |
| WO | WO 2006/133396 | 12/2006 |

OTHER PUBLICATIONS

Boon, 1992 (Adv Can Res, 58:177-210).*
Kirkin et al, 1998, APMIS, 106: 665-679.*
Smith RT, 1994 (Clin Immunol, 41(4): 841-849).*
Bodey et al, 2000, Anticancer Res, 20: 2665-2676.*
Lee et al, 1999, J Immunol, 163: 6292-6300.*
Bowie (Science, 1990, 257:1306-1310).*
Burgess et al ( J of Cell Bio. 111:2129-2138, 1990).*
Lazar et al (Molecular and Cellular Biology, 1988, 8:1247-1252).*
MPSRCH search result, 2008, us-11-245-713.1.rai, result 11, pp. 1-2.*
Bodey (Expert Opinion Biological Therapy, 2001, 1(4):603-17).*
Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
Montesano, R et al,1996, Intl J Cancer, 69(3): 225-235.*
Burmer, GC et al, 1991, Environmental Health perspectives, 93: 27-31.*
Busken, C et al, Digestive Disease Week Abstracts and Itinerary Planner, 2003, abstract No. 850.*
Stites et al, 1997, Medical Immunology, 9th ed., Appleton & Lange, Stamford, Connecticut, p. 123, 635.*
Mellman, 2006, The Scientist, 20(1): 47-56.*
Kaiser, 2006, Science, 313: 1370.*
Zips et al, 2005, In vivo, 19: 1-8.*
Experimental data generated by a licensee of the present application.
European Search Report for EP 05 80 8659, completed Mar. 25, 2009.
Thompson et al, "Costimulatory molecule B7-H1 in primary and metastatic clear cell renal cell carcinoma," Cancer. Nov. 15, 2005;104(10):2084-91.
Ohigashi et al. "Clinical significance of programmed death-1 ligand-1 and programmed death-1 ligand-2 expression in human esophageal cancer." Clin Cancer Res. Apr. 15, 2005;11(8):2947-53.
Iwai et al. "Involvement of PD-L1 on tumor cells in the escape from host immune system and tumor immunotherapy by PD-L1 blockade." Proc Natl Acad Sci U S A. Sep. 17, 2002;99(19):12293-7.
Curiel et al. "Blockade of B7-H1 improves myeloid dendritic cell—mediated antitumor immunity." Nat Med. May 2003;9(5):562-7.
Strome et al. "B7-H1 blockade augments adoptive T-cell immunotherapy for squamous cell carcinoma." Cancer Res. Oct. 1, 2003;63(19): 6501-5.
Zhang et al, "B7-H1-targeted immunotherapy for head and neck cancer." Expert Opinion on Biological Therapy Oct. 2004, vol. 4, No. 10 : pp. 1577-1583.
Hirano et al. "Blockade of B7-H1 and PD-1 by monoclonal antibodies potentiates cancer therapeutic immunity," Cancer Res. Feb. 1, 2005;65(3):1089-96.
He et al. "Blockade of B7-H1 with sPD-1 Improves Immunity against Murine Hepatocarcinoma." Anticancer Research Sep. 1, 2005 vol. 25 No. 5 3309-3313.
Thompson et al. "B7-H1 glycoprotein blockade: A novel strategy to enhance immunotherapy in patients with renal cell carcinoma." Urology, vol. 66, Issue 5, pp. 10-14.
Mazanet et al. "B7-H1 Is Expressed by Human Endothelial Cells and Suppresses T Cell Cytokine Synthesis." The Journal of Immunology, 2002, 169: 3581-3588.
Thompson et al. "Costimulatory B7-H1 in renal cell carcinoma patients:Indicator of tumor aggressiveness and potentialtherapeutic target." Proc Natl Acad Sci U S A. Dec. 7, 2004;101(49)17174-9.
Thompson et al. Implications of B7-H1Expression in Clear Cell Carcinoma of theKidney for Prognostication andTherapy. Clinical Cancer Research Jan. 15, 2007, 13, 709s.

(Continued)

*Primary Examiner*—Misook Yu
*Assistant Examiner*—Minh-Tam Davis
(74) *Attorney, Agent, or Firm*—Millen, White, Zelano, Branigan, P.C.

(57) ABSTRACT

The invention features methods of diagnosis by assessing B7-H1 expression in a tissue from a subject that has, or is suspected of having, cancer, methods of treatment with agents that interfere with B7-H1-receptor interaction, methods of selecting candidate subjects likely to benefit from cancer immunotherapy, and methods of inhibiting expression of B7-H1.

22 Claims, 6 Drawing Sheets

OTHER PUBLICATIONS

IDS submitted in U.S. Appl. No. 10/890,789 concerning certain test data (submited on Nov. 6, 2007).

Clinical Trials Database on phase I clinical trials using an anti-hB7-H1 monoclonal antibody (ID No. NCT00729664).

Ghebeh et al. "The B7-H1 (PD-L1) T Lymphocyte—Inhibitory Molecule Is Expressed in Breast Cancer Patients with Infiltrating Ductal Carcinoma:Correlation with Important High-Risk Prognostic Factors." (Neoplasia. Mar. 2006; 8(3): 190-198).

Konishi et al. "B7-H1 Expression on Non-Small Cell Lung Cancer Cells and Its Relationship with Tumor-Infiltrating Lymphocytes and Their PD-1 Expression." (Clin Cancer Res 10, 5094-5100, 2004).

Thompson et al. "Costimulatory B7-H1 in renal cell carcinoma patients." (Proc Natl Acad Sci USA 101, 17174-17179, 2004).

Ohigashi et al. "Clinical Significance of Programmed Death-1 Ligand-1 and Programmed Death-1 Ligand-2 Expression in Human Esophageal Cancer." (Clin Cancer Res 11, 2947-2953).

Brahmer et al. (J Clin Oncol 26: May 20, 2008, suppl; abstr 3006).

Melero et al. "Palettes of Vaccines and Immunostimulatory Monoclonal Antibodies." (Clinical Cancer Research, 2009).

Steinman et al. "Immunotherapy: Bewitched, Bothered, and Bewildered No More." (Science, 305, 197-200, 2004).

ASCO 2010 Press Release "Ipilimumab Improves Survival for Patients with Metastatic Melanoma." ASCO Meeting, Jun. 2010.

Hodi et al. "Re-induction with ipilimumab, gp100 peptide vaccine, or acombination of both from a phase III, randomized, double blind, multicenter study of previously treated patients with unresectable stage III or IV melanoma." J Clin Oncol 28:15s, 2010 (suppl; abstr 8509).

Lawrence et al. "Phase II trial of ipilimumab monotherapy in melanoma." J Clin Oncol 28:15s, 2010 (suppl; abstr 8523).

FDA News Release "FDA Approves a Cellular Immunotherapy for Men with Advanced Prostate Cancer." Apr. 29, 2010.

\* cited by examiner

FIG. 3

MRIFAVFIFMTYWHLLNAFTVTVPKDLYVVEYGSNMTIECKFPVEKQLDLAALIV
YWEMEDKNIIQFVHGEEDLKVQHSSYRQRARLLKDQLSLGNAALQITDVKLQD
AGVYRCMISYGGADYKRITVKVNAPYNKINQRILVVDPVTSEHELTCQAEGYPK
AEVIWTSSDHQVLSGKTTTTNSKREEKLFNVTSTLRINTTTNEIFYCTFRRLDPEE
NHTAELVIPELPLAHPPNERTHLVILGAILLCLGVALTFIFRLRKGRMMDVKKCGI
QDTNSKKQSDTHLEET

FIG. 4

ATGAGGATATTTGCTGTCTTTATATTCATGACCTACTGGCATTTGCTGAACGC
ATTTACTGTCACGGTTCCCAAGGACCTATATGTGGTAGAGTATGGTAGCAATA
TGACAATTGAATGCAAATTCCCAGTAGAAAAACAATTAGACCTGGCTGCACT
AATTGTCTATTGGGAAATGGAGGATAAGAACATTATTCAATTTGTGCATGGA
GAGGAAGACCTGAAGGTTCAGCATAGTAGCTACAGACAGAGGGCCCGGCTG
TTGAAGGACCAGCTCTCCCTGGGAAATGCTGCACTTCAGATCACAGATGTGA
AATTGCAGGATGCAGGGGTGTACCGCTGCATGATCAGCTATGGTGGTGCCGA
CTACAAGCGAATTACTGTGAAAGTCAATGCCCCATACAACAAAATCAACCAA
AGAATTTTGGTTGTGGATCCAGTCACCTCTGAACATGAACTGACATGTCAGGC
TGAGGGCTACCCCAAGGCCGAAGTCATCTGGACAAGCAGTGACCATCAAGTC
CTGAGTGGTAAGACCACCACCACCAATTCCAAGAGAGAGGAGAAGCTTTTCA
ATGTGACCAGCACACTGAGAATCAACACAACAACTAATGAGATTTTCTACTG
CACTTTTAGGAGATTAGATCCTGAGGAAAACCATACAGCTGAATTGGTCATC
CCAGAACTACCTCTGGCACATCCTCCAAATGAAAGGACTCACTTGGTAATTCT
GGGAGCCATCTTATTATGCCTTGGTGTAGCACTGACATTCATCTTCCGTTTAA
GAAAAGGGAGAATGATGGATGTGAAAAAATGTGGCATCCAAGATACAAACT
CAAAGAAGCAAAGTGATACACATTTGGAGGAGACG

FIG. 5

MRIFAGIIFTACCHLLRAFTITAPKDLYVVEYGSNVTMECRFPVERELDLLALVV
YWEKEDEQVIQFVAGEEDLKPQHSNFRGRASLPKDQLLKGNAALQITDVKLQDA
GVYCCIISYGGADYKRITLKVNAPYRKINQRISVDPATSEHELICQAEGYPEAEVI
WTNSDHQPVSGKRSVTTSRTEGMLLNVTSSLRVNATANDVFYCTFWRSQPGQN
HTAELIIPELPATHPPQNRTHWVLLGSILLFLIVVSTVLLFLRKQVRMLDVEKCGV
EDTSSKNRNDTQFEET

FIG. 6

ATGAGGATATTTGCTGGCATTATATTCACAGCCTGCTGTCACTTGCTACGGGC
GTTTACTATCACGGCTCCAAAGGACTTGTACGTGGTGGAGTATGGCAGCAAC
GTCACGATGGAGTGCAGATTCCCTGTAGAACGGGAGCTGGACCTGCTTGCGT
TAGTGGTGTACTGGGAAAAGGAAGATGAGCAAGTGATTCAGTTTGTGGCAGG
AGAGGAGGACCTTAAGCCTCAGCACAGCAACTTCAGGGGGAGAGCCTCGCT
GCCAAAGGACCAGCTTTTGAAGGGAAATGCTGCCCTTCAGATCACAGACGTC
AAGCTGCAGGACGCAGGCGTTTACTGCTGCATAATCAGCTACGGTGGTGCGG
ACTACAAGCGAATCACGCTGAAAGTCAATGCCCCATACCGCAAAATCAACCA
GAGAATTTCCGTGGATCCAGCCACTTCTGAGCATGAACTAATATGTCAGGCC
GAGGGTTATCCAGAAGCTGAGGTAATCTGGACAAACAGTGACCACCAACCCG
TGAGTGGGAAGAGAAGTGTCACCACTTCCCGGACAGAGGGGATGCTTCTCAA
TGTGACCAGCAGTCTGAGGGTCAACGCCACAGCGAATGATGTTTTCTACTGT
ACGTTTTGGAGATCACAGCCAGGGCAAAACCACACAGCGGAGCTGATCATCC
CAGAACTGCCTGCAACACATCCTCCACAGAACAGGACTCACTGGGTGCTTCT
GGGATCCATCCTGTTGTTCCTCATTGTAGTGTCCACGGTCCTCCTCTTCTTGAG
AAAACAAGTGAGAATGCTAGATGTGGAGAAATGTGGCGTTGAAGATACAAG
CTCAAAAAACCGAAATGATACACAATTCGAGGAGACG

SEQUENCE LISTING

<160> NUMBER OF SEQ ID NOS: 4

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 870
<212> TYPE: DNA
<213> ORGANISM: Homo sapiens

<400> SEQUENCE: 2
atgaggatat tgctgtgtctt tatattcatg acctactggc atttgctgaa cgcatttact      60

```
gtcacggttc caaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aggactcac     720 ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg atacacattt ggaggagacg                                      870

<210> SEQ ID NO 3
<211> LENGTH: 290
<212> TYPE: PRT
<213> ORGANISM: Mus musculus

<400> SEQUENCE: 3

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
```

-continued

```
                 225                 230                 235                 240
Val Leu Leu Gly Ser Ile Leu Leu Phe Leu Ile Val Val Ser Thr Val
                    245                 250                 255
Leu Leu Phe Leu Arg Lys Gln Val Arg Met Leu Asp Val Glu Lys Cys
                260                 265                 270
Gly Val Glu Asp Thr Ser Ser Lys Asn Arg Asn Asp Thr Gln Phe Glu
            275                 280                 285
Glu Thr
    290

<210> SEQ ID NO 4
<211> LENGTH: 870
<212> TYPE: DNA
<213> ORGANISM: Mus musculus

<400> SEQUENCE: 4
atgaggatat  ttgctggcat  tatattcaca  gcctgctgtc  acttgctacg  ggcgtttact     60
atcacggctc  caaaggactt  gtacgtggtg  gagtatggca  gcaacgtcac  gatggagtgc    120
agattccctg  tagaacggga  gctggacctg  cttgcgttag  tggtgtactg  ggaaaaggaa    180
gatgagcaag  tgattcagtt  tgtggcagga  gaggaggacc  ttaagcctca  gcacagcaac    240
ttcaggggga  gagcctcgct  gccaaaggac  cagcttttga  agggaaatgc  tgcccttcag    300
atcacagacg  tcaagctgca  ggacgcaggc  gtttactgct  gcataatcag  ctacggtggt    360
gcggactaca  agcgaatcac  gctgaaagtc  aatgccccat  accgcaaaat  caaccagaga    420
atttccgtgg  atccagccac  ttctgagcat  gaactaatat  gtcaggccga  gggttatcca    480
gaagctgagg  taatctggac  aaacagtgac  caccaacccg  tgagtgggaa  gagaagtgtc    540
accacttccc  ggacagaggg  gatgcttctc  aatgtgacca  gcagtctgag  ggtcaacgcc    600
acagcgaatg  atgttttcta  ctgtacgttt  tggagatcac  agccagggca  aaaccacaca    660
gcggagctga  tcatcccaga  actgcctgca  acacatcctc  cacagaacag  gactcactgg    720
gtgcttctgg  gatccatcct  gttgttcctc  attgtagtgt  ccacggtcct  cctcttcttg    780
agaaaacaag  tgagaatgct  agatgtggag  aaatgtggcg  ttgaagatac  aagctcaaaa    840
aaccgaaatg  atacacaatt  cgaggagacg                                        870
```

B7-H1 AND METHODS OF DIAGNOSIS, PROGNOSIS, AND TREATMENT OF CANCER

This application claims the benefit of U.S. Provisional Application No. 60/616,590, filed Oct. 6, 2004, and U.S. Provisional Application 60/642,794, filed Jan. 11, 2005. The disclosures of U.S. Provisional Application No. 60/616,590 and U.S. Provisional Application 60/642,794 are incorporated herein by reference in their entirety.

TECHNICAL FIELD

This invention relates to immune molecules expressed in cancer tissue, and more particularly to evaluating the expression of immune molecules in tumor cells and tumor-infiltrating leukocytes.

BACKGROUND

An important determinant for the initiation and progression of cancer is the ability of cancer cells to evade the host's immune system. The presence in cancer tissue of, for example, inadequate, inappropriate, or inhibitory immune molecules can restrict the host's ability to generate immune responses to the cancer.

The disclosures of U.S. Pat. No. 6,803,192 and co-pending U.S. application Ser. Nos. 09/649,108; 10/127,282; and 10/719,477; and International Application No. US/02/32364 are incorporated herein by reference in their entirety.

SUMMARY

The invention is based in part on the finding that in renal cell carcinoma (RCC) patients the risk of death is proportional to the number of tumor cells, and/or leukocytes in the tumor, expressing the co-stimulatory human glycoprotein B7-H1. As used herein, the term "B7-H1" refers to B7-H1 from any mammalian species and the term "hB7-H1" refers to human B7-H1. Further details on B7-H1 polypeptides and nucleic acids are provided in U.S. Pat. No. 6,803,192 and co-pending U.S. application Ser. No. 09/649,108, the disclosures of which are incorporated herein by reference in their entirety.

The invention provides methods of diagnosing subjects having, or that are likely to develop, cancer of a tissue based on the expression of B7-H1 by cells of the cancer tissue, methods of predicting success of immunotherapy, methods of prognosis, and methods of treatment. Leukocytes in a tumor are sometimes referred to herein as "tumor-infiltrating leukocytes" or "leukocytes infiltrating a/the tumor."

More specifically, the invention provides a method of diagnosis of cancer in a subject. The method involves: (a) providing a tissue sample from a subject suspected of having, or likely to develop, cancer of the tissue, wherein the sample contains test cells, the test cells being cells of the tissue or leukocytes infiltrating the tissue; and (b) assessing whether the test cells express B7-H1, wherein expression by some or all of the test cells is an indication that the subject has cancer.

The assessment of B7-H1 expression can be performed by the detection of B7-H1 polypeptide or mRNA. B7-H1 polypeptide can be detected, for example, by contacting the tissue sample, or test cells contained in the tissue sample, with an antibody that binds to the B7-H1 polypeptide. Suitable methods for detection of B7-H1 polypeptide can include, without limitation, fluorescence flow cytometry (FFC) or immunohistology. B7-H1 mRNA can be detected, for example, by contacting the tissue sample with a nucleic acid probe that hybridizes to the B7-H1 mRNA (e.g., such by in situ hybridization) or by reverse transcriptase-polymerase chain reaction. The tissue can be tissue of any organ or anatomical system, and can include, without limitation, lung, epithelial, connective, vascular, muscle, neural, skeletal, lymphatic, prostate, cervical, breast, spleen, gastric, intestinal, oral, esophageal, uterine, ovarian, or testicular tissue. The tissue can also be renal tissue. The subject can be a mammal, such as, for example, a human.

Another aspect of the invention is a method of identifying a candidate for immunotherapy. This method involves: (a) providing a tissue sample from a subject with cancer of the tissue, wherein the tissue sample contains test cells, the test cells being cancer cells or tumor-infiltrating leukocytes; and (b) assessing the level of test cells in the tissue sample that express B7-H1, wherein, if B7-H1 expression is not detected in the test cells or if less than an immuno-inhibitory threshold level of the test cells express B7-H1, the subject is more likely to benefit from immunotherapy.

The level of B7-H1 can be assessed by detecting B7-H1 polypeptide or mRNA using, for example, any of the methods described above for method of diagnosis. The tissue can be tissue of any organ or anatomical system, and can include, without limitation, lung, epithelial, connective, vascular, muscle, neural, skeletal, lymphatic, prostate, cervical, breast, spleen, gastric, intestinal, oral, esophageal, uterine, ovarian, or testicular tissue. The tissue can also be renal tissue. The subject can be a mammal, such as, for example, a human. The cancer can be any cancer, and includes, for example, renal cell carcinoma.

In another embodiment, the invention features a method of determining the prognosis of a subject with cancer. This method involves: (a) providing a tissue sample from a subject with cancer of the tissue, wherein the tissue sample comprises test cells, the test cells being cancer cells or tumor-infiltrating leukocytes; and (b) assessing the level of test cells in the tissue sample that express B7-H1, wherein, if a prognostic level, or more than a prognostic level, of the test cells express B7-H1, the subject is more likely to die of the cancer than if less than a prognostic level of the test cells express B7-H1. The prognostic level is a predetermined value obtained by performing statistical clinical analyses known in the art, e.g., those described herein. The assessment of B7-H1 can be performed by detecting B7-H1 polypeptide or B7-H1 mRNA using any of a variety of methods known in the art, including, for example, those listed above for methods of diagnosis and method of immunotherapy. The tissue sample can be of any tissue, and can include, for example, any of those described above. The subject from which the tissue is provided can be a mammal, e.g., a human.

Yet another aspect of the invention is a method of treatment. The method involves: (a) identifying a subject with cancer, wherein some or all cells of the cancer or some or all tumor-infiltrating leukocytes of the cancer express B7-H1; and (b) delivering to the subject an agent that interferes with an interaction between B7-H1 and a receptor for B7-H1. The agent can bind to B7-H1 or to a receptor for B7-H1, e.g., the PD-1 receptor. The agent can be an antibody or an antibody fragment (e.g., Fab', F(ab')$_2$, or single chain Fv (scFv) fragment) that binds to B7-H1 or binds to a receptor for B7-H1; soluble B7-H1 or a soluble functional fragment of B7-H1; a soluble receptor for B7-H1 or a soluble functional fragment thereof. Whenever it is desired, the agent can be administered before, simultaneous with, or after administration of one or more immunomodulatory cytokines, growth factors, or anti-angiogenic factors. Examples of such immunomodulatory cytokines, growth factors, and antiangiogenic factors include, without limitation, any of interleukins (IL)-1 to 25, interferon-γ (IFN-γ), interferon-α (IFN-α), interferon-β (IFN-β), interferon-γ (IFN-γ), tumor necrosis factor-α (TNF-α), granulocyte macrophage colony stimulating factor (GM-CSF), granulocyte macrophage colony stimulating factor (G-CSF), endostatin, angiostatin, and thrombospondin. Administrations of the agent and/or the one or more immunomodulatory cytokines, growth factors, or antiangiogenic factors can be systemic (e.g., intravenous) or local, e.g., during surgery by direct injection or infusion into the tissue that comprises the cells of the cancer and/or tumor-infiltrating leukocytes. The cancer can be, without limitation, hematological cancer, neurological cancer, melanoma, breast cancer, lung cancer, head and neck cancer, gastrointestinal cancer, liver cancer, pancreatic cancer, renal cancer, genitourinary cancer, bone cancer, or vascular cancer.

Yet another aspect of the invention is a method of inhibiting the expression of B7-H1 in a tumor cell or a tumor-infiltrating leukocyte. The method involves: (a) identifying a subject with cancer, the cancer containing a target cell that expresses B7-H1, the target cell being a tumor cell or a tumor-infiltrating leukocyte; and (b) introducing into the target cell: (i) an antisense oligonucleotide that hybridizes to a B7-H1 transcript, wherein the antisense oligonucleotide inhibits the expression of B7-H1 in the cell; or (ii) a B7-H1 interference RNA (RNAi). The introducing step can involve administration of the antisense oligonucleotide or the RNAi to the subject and uptake of the oligonucleotide or the RNAi by the target cell. Alternatively, the introducing step can involve administering to the subject, and uptake by the cell of, a nucleic acid comprising a transcriptional regulatory element (TRE) operably linked to a nucleotide sequence complementary to the antisense oligonucleotide, wherein transcription of the nucleotide sequence inside the cell produces the antisense oligonucleotide. Moreover, the introducing step can include administering to the subject, and uptake by the cell of, a nucleic acid: (a) from which sense and anti-sense strands of the RNAi can be transcribed under the direction of the TREs; or (b) from which both sense and anti-sense strands of the RNAi can be transcribed under the direction of a single TRE.

The tissue sample can be lung, epithelial, connective, vascular, muscle, neural, skeletal, lymphatic, prostate, cervical, breast, spleen, gastric, intestinal, oral, esophageal, dermal, liver, bladder, thyroid, thymic, adrenal, brain, gallbladder, pancreatic, uterine, ovarian, or testicular tissue. The tissue can also be renal tissue. The cancer of the tissue can be any cancer and includes, e.g., renal cell carcinoma.

The subject can be a mammal and includes, for example, a human, a non-human primate (e.g., a monkey), a horse, a cow (or an ox or bull), a pig, a sheep, a goat, a cat, a rabbit, a guinea pig, a hamster, a rat, or a gerbil.

As used herein, "interferes with an interaction between B7-H1 and a receptor for B7-H1" means (a) completely blocks a physical interaction between B7-H1 molecule and a receptor for B7-H1 such that there is substantially no physical interaction between the B7-H1 molecule and the receptor; or (b) modifies the interaction between the B7-H1 molecule and the receptor such that the physical interaction either does not deliver a signal to the cell that comprises B7-H1, and/or the receptor for B7-H1, or delivers a signal that does not substantially affect the antitumoral activity of the cell.

"Polypeptide" and "protein" are used interchangeably and mean any peptide-linked chain of amino acids, regardless of length or post-translational modification. Polypeptides useful for the invention include variant polypeptides that are identical to corresponding wild-type polypeptides but differ by not more than 50 (e.g., not more than: 45; 40; 35; 30; 25; 20; 19; 18; 17; 16; 15; 14; 13; 12; 11; 10; nine; eight; seven; six; five; four; three; two; or one) conservative substitution(s). All that is required is that the variant polypeptide has at least 20% (e.g., at least: 25%; 30%; 35%; 40%; 45%; 50%; 60%; 70%; 80%; 85%; 90%; 93%; 95%; 96%; 97%; 98%; 99%; 99.5%; 99.8%; 99.9%; or 100% or more) of the activity of the wild-type polypeptide. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine.

As used herein, "tumor-infiltrating leukocytes" can be T lymphocytes (such as $CD8^+$ T lymphocytes and/or $CD4^+$ T lymphocytes), B lymphocytes, or other bone marrow-lineage cells including granulocytes (neutrophils, eosinophils, basophils), monocytes, macrophages, dendritic cells (i.e., interdigitating dendritic cells), histiocytes, and natural killer cells.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention will be apparent from the following description, from the drawings and from the claims.

DESCRIPTION OF DRAWINGS

FIG. 2A shows the association of tumor hB7-H1 expression with death from RCC (risk ratio 2.91; 95% CI [Confidence Interval] 1.39-6.13; p=0.005). The cancer-specific survival rates (with standard error [SE] and number still at risk indicated in parentheses) at 1, 2, and 3 years following nephrectomy were: 87.8% (4.1%, 53), 72.3% (6.0%, 30), and 63.2% (7.2%, 11), respectively, for patients with specimens that had ≧10% tumor hB7-H1 expression; compared with 93.6% (2.3%, 95), 88.4% (3.4%, 48), and 88.4% (3.4%, 19), respectively, for patients with specimens that had <10% tumor hB7-H1 expression.

FIG. 2B shows the association of adjusted score for leukocyte hB7-H1 expression with death from RCC (risk ratio 3.58; 95% CI 1.74-7.37; p<0.001). The cancer-specific survival rates (SE, number still at risk) at 1, 2, and 3 years were: 83.5% (6.2%, 26), 63.9% (9.2%, 13), and 53.6% (10.2%, 5), respectively, for patients with specimens that had a leukocyte hB7-H1 expression score ≧100; compared with 93.5%

(2.1%, 122), 86.2% (3.3%, 65), and 84.8% (3.5%, 25), respectively, for patients with specimens that had scores <100.

Figure 2:
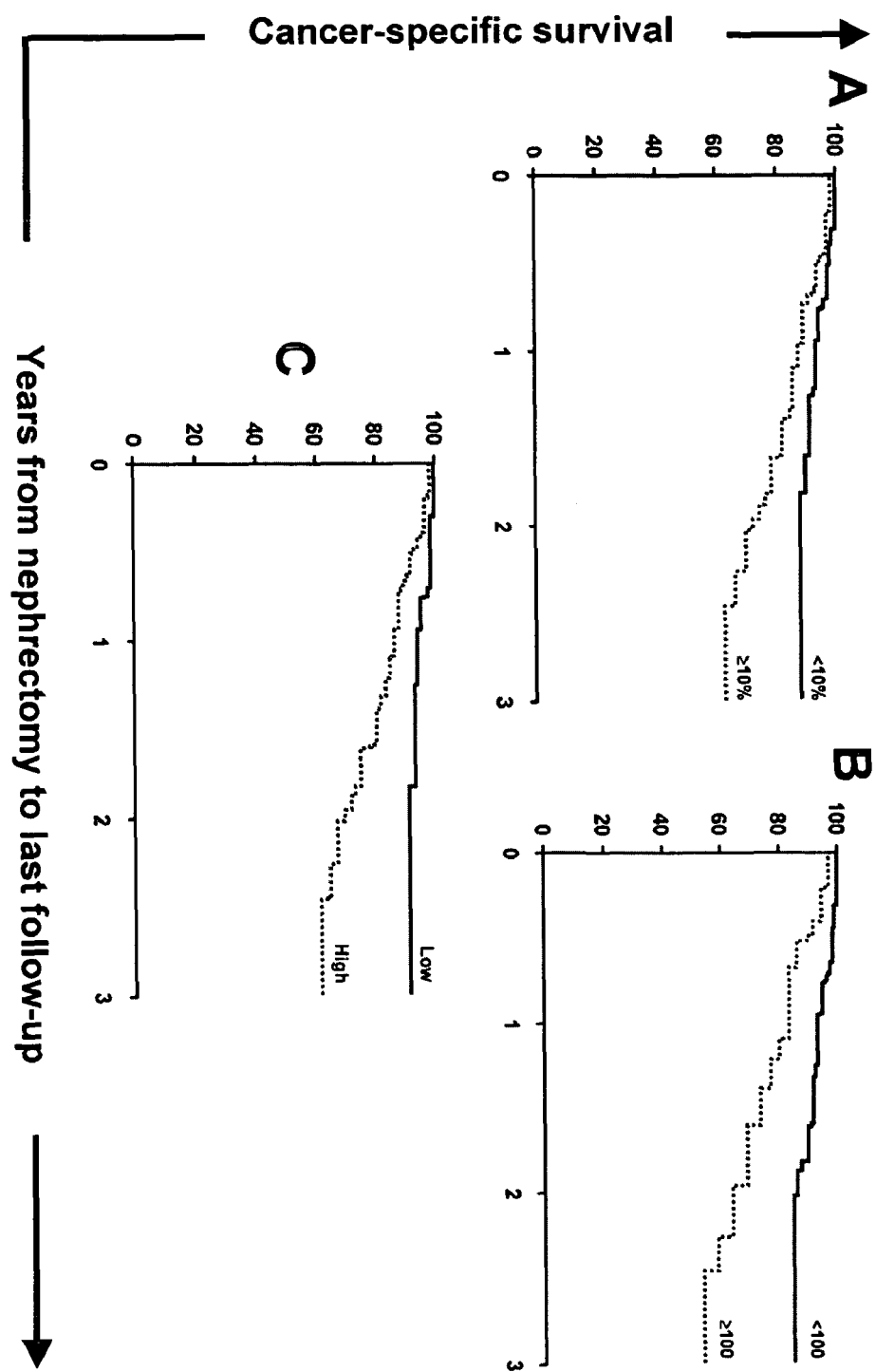
FIG. 2 is a series of line graphs showing the associations of hB7-H1 expression with death from RCC in 196 subjects from whom the clear cell RCC specimens were obtained for analysis.

FIG. 2C shows the association of high aggregate intratumoral hB7-H1 expression with death from RCC (risk ratio 4.53; 95% CI 1.94-10.56; p<0.001). The cancer-specific survival rates (SE, number still at risk) at 1, 2, and 3 years were: 87.0% (3.8%, 61), 70.0% (5.8%, 32), and 61.9% (6.8%, 13), respectively, for patients with specimens that had high aggregate intratumoral hB7-H1 expression; compared with 94.9% (2.2%, 87), 91.9% (3.1%, 46), and 91.9% (3.1%, 17), respectively, for patients with specimens that had both <10% tumor and <100 leukocyte (low aggregate intratumoral expression) hB7-H1 expression.

FIG. 3 is a depiction of the amino acid sequence (SEQ ID NO:1) of full-length, immature hB7-H1, i.e., hB7-H1 including a leader peptide of about 22 amino acids.

FIG. 4 is a depiction of the nucleotide sequence (SEQ ID NO:2) of cDNA encoding full-length, immature hB7-H1.

FIG. 5 is a depiction of the amino acid sequence (SEQ ID NO:3) of full-length, immature murine B7-H1.

FIG. 6 is a depiction of the nucleotide sequence (SEQ ID NO:4) of cDNA encoding full-length, immature murine B7-H1.

DETAILED DESCRIPTION

The inventors have discovered that renal cell carcinoma (RCC) patients who have increased levels of tumor cells and/or tumor-infiltrating leukocytes expressing the costimulatory glycoprotein hB7-H1 are at an increased risk of death from the RCC. In addition, elevated levels of hB7-H1 expressing tumor cells and/or tumor-infiltrating leukocytes was associated with more aggressive tumors and this association persisted even after controlling for traditional predictors of RCC progression, including, for example, tumor, node, metastasis (TNM) stage; primary tumor size; nuclear grade; and histological tumor necrosis.

Expression of B7-H1 in normal, non-activated mammalian cells is largely, if not exclusively, limited to macrophage-lineage cells and provides a potential costimulatory signal source for regulation of T cell activation. In contrast, aberrant expression of B7-H1 by tumor cells has been implicated in impairment of T cell function and survival, resulting in defective host antitumoral immunity.

The inventors found that human RCC tumors express hB7-H1. In particular, hB7-H1 was found to be expressed by both renal cell carcinoma (RCC) tumors and leukocytes infiltrating RCC tumors. In contrast, proximal tubules of the renal cortex, from which clear cell tumors are believed to arise, failed to express hB7-H1.

Clinical specimens were obtained from 196 patients who were treated with radical nephrectomy or nephron-sparing surgery for unilateral, clear cell RCC between 2000 and 2002 from the Mayo Clinic Nephrectomy Registry. Immunohistological detection and quantification of hB7-H1 expression in the specimens revealed that patients whose tumor specimens exhibited high intratumoral expression levels of hB7-H1 (contributed by tumor cells alone, leukocytes alone, or tumor and/or leukocytes combined) had aggressive tumors and were at markedly increased risk of death from RCC.

The combination of increased tumor cell hB7-H1 and tumor-infiltrating leukocyte hB7-H1 (high aggregate intratumoral hB7-H1) was an even stronger predictor of patient outcome than either hB7-H1-expressing tumor cells or tumor-infiltrating leukocytes alone. High aggregate intratumoral hB7-H1 expression levels were also significantly associated with regional lymph node involvement, distant metastases, advanced nuclear grade, and the presence of histologic tumor necrosis.

Based on its ability to impair function and survival of activated tumor-specific T cells, B7-H1, expressed by either tumor cells (e.g., RCC cells) or infiltrating leukocytes, can contribute to the immunosuppression that is commonly observed in subjects with cancer (e.g., RCC) and can serve as a critical determinant of the subjects' responses to immunotherapy for management of advanced cancer (e.g., IL-2, IL-12, IFN-α, vaccination or T-cell adoptive therapy). This raises the possibility that administering to cancer patients agents that interfere with the interaction of B7-H1 with its receptor (e.g., PD-1) can serve as a method of immunotherapy, particularly in subjects whose high level of intratumoral B7-H1 expression previously rendered them unresponsive or nearly unresponsive to other modes of immunotherapy.

These findings provide support for the methods of the invention, which are described below.

Methods of Diagnosis

The invention provides a method of diagnosing cancer in a subject. The method involves: (a) providing a tissue sample from a subject suspected of having, or likely to develop, cancer of the tissue, the sample containing test cells, the test cells being cells of the tissue or leukocytes infiltrating the tissue; and (b) assessing whether the test cells express B7-H1. Expression by some or all of the test cells is an indication that the subject has cancer. Since a wide variety of cancer cells express B7-H1 on their surfaces, the methods of the invention are particularly useful for diagnosing any such cancer. Test cells can thus be, for example, breast cells, lung cells, colon cells, pancreatic cells, renal cells, stomach cells, liver cells, bone cells, hematological cells (e.g., lymphoid cells, granulocytic cells, monocytes or macrophages), neural tissue cells, melanocytes, ovarian cells, testicular cells, prostate cells, cervical cells, vaginal cells, bladder cells, or any other cells listed herein. Moreover, test cells can be leukocytes present in relevant tissues containing any of the above-listed test cells. Leukocytes infiltrating the tissue can be T cells (CD4$^+$ T cells and/or CD8$^+$ T cells) or B lymphocytes. Such leukocytes can also be neutrophils, eosinophils, basophils, monocytes, macrophages, histiocytes, or natural killer cells. Subjects can be mammals and include, for example, humans, non-human primates (e.g., monkeys, baboons, or chimpanzees), horses, cows (or oxen or bulls), pigs, sheep, goats, cats, rabbits, guinea pigs, hamsters, rats, gerbils, or mice.

As described herein, the invention provides a number of diagnostic advantages and uses. In the methods of the invention, the level of B7-H1 polypeptide and/or mRNA can be assessed. The level of B7-H1 is assessed in a tissue sample to diagnose, or to confirm, the presence of cancer in the subject from whom the tissue is obtained.

Methods of detecting a polypeptide in a tissue sample are known in the art. For example, antibodies (or fragments thereof) that bind to an epitope specific for B7-H1 can be used to assess whether test cells from the tissue sample express B7-H1. Such antibodies can be monoclonal or polyclonal antibodies. In such assays, the antibody itself, or a secondary antibody that binds to it, can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-detecting assays (e.g., ELISA or Western blot) can be applied to lysates of cells, and others (e.g., immunohistological methods or fluorescence flow cytometry) can be applied to histological sections or unlysed cell suspensions. The tissue sample can be, for example, lung, epithelial, connective, vascular, muscle, neural, skeletal, lymphatic, prostate, cervical, breast, spleen, gastric, intestinal, oral, esophageal, dermal, liver, kidney, bladder, thyroid, adrenal, brain, gallbladder, pancreatic, uterine, ovarian, or testicular tissue.

Methods of detecting an mRNA in a tissue sample are known in the art. For example, cells can be lysed and an mRNA in the lysates or in RNA purified or semi-purified from the lysates can be detected by any of a variety of methods including, without limitation, hybridization assays using detectably labeled gene-specific DNA or RNA probes (e.g., Northern Blot assays) and quantitative or semi-quantitative RT-PCR methodologies using appropriate gene-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of assessing the level of B7-H1 expression (RNA and/or polypeptide) can be can be quantitative, semi-quantitative, or qualitative. Thus, for example, the level of B7-H1 expression can be determined as a discrete value. For example, where quantitative RT-PCR is used, the level of expression of B7-H1 mRNA can be measured as a numerical value by correlating the detection signal derived from the quantitative assay to the detection signal of a known concentration of: (a) B7-H1 nucleic acid sequence (e.g., B7-H1 cDNA or B7-H1 transcript); or (b) a mixture of RNA or DNA that contains a nucleic acid sequence encoding B7-H1. Alternatively, the level of B7-H1 expression can be assessed using any of a variety of semi-quantitative/qualitative systems known in the art. Thus, the level of expression of B7-H1 in a cell or tissue sample can be expressed as, for example, (a) one or more of "excellent", "good", "satisfactory", "unsatisfactory", and/or "poor"; (b) one or more of "very high", "high", "average", "low", and/or "very low"; or (c) one or more of "++++", "+++", "++", "+", "+/−", and/or "−". Where it is desired, the level of expression of B7-H1 in tissue from a subject can be expressed relative to the expression of B7-H1 from (a) a tissue of a subject known not to be cancerous (e.g., a contralateral kidney or lung, or an uninvolved lymph node); or (b) a corresponding tissue from one or more other subjects known not to have the cancer of interest, preferably known not to have any cancer.

Methods of assessing the amount of label depend on the nature of the label and are well known in the art. Appropriate labels include, without limitation, radionuclides (e.g., $^{125}$I, $^{131}$I, $^{35}$S, $^3$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, green fluorescent protein (GFP), or blue fluorescent protein (BFP)), or luminescent moieties (e.g., Qdot™ nanoparticles supplied by the Quantum Dot Corporation, Palo Alto, Calif.). Other applicable assays include quantitative immunoprecipitation or complement fixation assays.

In the diagnostic assays of the invention, a subject is diagnosed as having cancer if the proportion of test cells from the subject that express B7-H1 is greater than a control value. The control value, can be, for example: (a) the proportion of B7-H1-expressing cells in corresponding tissue of the subject known not be cancerous (e.g., a contralateral kidney or lung, or an uninvolved lymph node); or (b) the proportion of B7-H1 expressing cells in a corresponding tissue from one or more other subjects known not to have the cancer of interest, preferably known not to have any cancer.

The method of the invention can be used on its own or in conjunction with other procedures to diagnose cancer. For example, where it is desired or preferred, the level of B7-H1-expressing test cells in a tissue sample that is, or is suspected of being, cancerous can be assessed before, during, or after assessing the levels of other molecules that are useful diagnostic cancer markers. Such diagnostic markers can be, without limitation, tumor-associated antigens (TAA). Relevant TAA include, without limitation, carcinoembryonic antigen (CEA), MAGE (melanoma antigen) 1-4, 6, and 12, MUC (mucin) (e.g., MUC-1, MUC-2, etc.), tyrosinase, MART (melanoma antigen), Pmel 17 (gp100), GnT-V intron sequence (N-acetylglucosaminyltransferase V intron V sequence), PSA (prostate-specific antigen), PSMA (prostate-specific membrane antigen), PRAME (melanoma antigen), β-catenin, MUM-1-B (melanoma ubiquitous mutated gene product), GAGE (melanoma antigen) 1, BAGE (melanoma antigen) 2-10, c-ERB2 (HER2/neu), EBNA (Epstein-Barr Virus nuclear antigen) 1-6, gp75, human papilloma virus (HPV) E6 and E7, p53m lung resistance protein (LRP), Bcl-2, Ki-67, and VHL (von Hippel-Lindau) gene.

Method of Identifying Cancer Subjects Likely to Benefit from Immunotherapy

Another aspect of the invention is a method of identifying a candidate for immunotherapy. This method involves providing a tissue sample from a subject with cancer of the tissue. The tissue sample contains test cells, the test cells being cancer cells or tumor-infiltrating leukocytes. The level of test cells in the tissue sample that express B7-H1 is assessed, such that if B7-H1 expression is not detected in the test cells, or less than an immuno-inhibitory threshold level of the test cells express B7-H1, the subject is more likely to benefit from immunotherapy.

The immuno-inhibitory threshold level is a predetermined level of the relevant test cells expressing B7-H1. If the test cells from a cancer subject of interest contain a level of B7-H1-expressing cells that is less than the immuno-inhibitory threshold level of B7-H1-expressing cells (as predetermined for the relevant cancer), that subject is more likely to benefit from immunotherapy than another subject with the same cancer but whose corresponding test cells contain a level of B7-H1-expressing cells equal to, or greater than, the immuno-inhibitory threshold level. The immuno-inhibitory threshold level can be obtained by performing statistical clinical analyses known in the art, e.g., those described herein.

Methods of assessing whether test cells express B7-H1 are the same as those described above for methods of diagnosis. Such methods, also as described above, can be qualitative, semi-quantitative, or qualitative.

"Immunotherapy" can be active immunotherapy or passive immunotherapy. For active immunotherapy, treatment relies on the in vivo stimulation of the endogenous host immune system to react against tumors with the administration of immune response-modifying agents. These immune-response-modifying agents are described below.

For passive immunotherapy, treatment involves the delivery of agents with established tumor-immune reactivity (such as immune effector cells or antibodies) that can directly, or indirectly mediate, anti-tumor effects and do not necessarily depend on an intact host immune system. Examples of immune effector cells include leukocytes, e.g., tumor-infiltrating leukocytes as discussed above, T lymphocytes (such as CD8$^+$ cytotoxic T lymphocytes and/or CD4$^+$ T-helper lymphocytes), killer cells (such as natural killer cells and lymphokine-activated killer cells), B cells and antigen-presenting cells (such as dendritic cells and macrophages).

Immunotherapy can also be one or more of the methods described below (in "Methods of Treatment" and "Methods of Inhibiting Expression of B7-H1).

Method of Prognosis

In another embodiment, the invention features a method of determining the prognosis of a subject with cancer. This method involves: (a) providing a tissue sample from a subject with cancer of the tissue, the tissue sample containing test cells, the test cells being cancer cells or tumor infiltrating leukocytes; and (b) assessing the level of test cells in the tissue sample that expresses B7-H1. If a prognostic level, or more than a prognostic level, of the test cells express B7-H1, the subject is more likely to die of the cancer than if less than a prognostic level of the test cells express B7-H1. The prognostic level is a predetermined value obtained by performing statistical clinical analyses known in the art, e.g., those described herein.

Thus, for example, if test cells from a cancer subject contain a significant level of B7-H1 expressing cells, but less than a prognostic level of B7-H1-expressing cells (as predetermined for the relevant cancer), the cancer subject will be no more likely to die of the cancer than a subject with the same cancer but whose corresponding test cells contain no detectable B7-H1-expressing cells. On the other hand, if test cells from a cancer subject contain more than a prognostic level of B7-H1-expressing cells, the cancer subject will be more likely to die of the cancer than a subject with the same cancer but whose corresponding test cells contain either no detectable B7-H1-expressing cells or a level of B7-H1-expressing cells lower than a prognostic level of B7-H1-expressing cells. Moreover, for subjects with cancer having levels of B7-H1-expressing cells in appropriate test cell populations greater than prognostic levels, the chances of dying from the cancer is likely to be proportional to the level of B7-H1-expressing cells in the test cell population.

As used herein, "assessing whether test cells express B7-H1" or "assessing the level of test cells in the tissue sample that express B7-H1" can be determined by any of the methods described above. Methods of prognosis will generally be quantitative or semi-quantitative.

Subjects can be any of those listed for "Methods of Diagnosis" and cancers can be any of the following: renal cancer, hematological cancer (e.g., leukemia or lymphoma), neurological cancer, melanoma, breast cancer, lung cancer, head and neck cancer, gastrointestinal cancer, liver cancer, pancreatic cancer, pancreatic cancer, genitourinary cancer, bone cancer, or vascular cancer Methods of Treatment The invention also includes a method of treatment. The method can involve: (a) identifying a subject with cancer, some or all cells of the cancer or some or all tumor-infiltrating leukocytes of the cancer expressing B7-H1; and (b) delivering to the subject an agent that interferes with an interaction between B7-H1 and a receptor for B7-H1. These methods can be performed subsequent to, or without, performing any of the above-described methods. The agent can be an antibody or an antibody fragment, such as, e.g., a Fab', a F(ab')$_2$, or a scFv fragment that binds B7-H1. The agent can also be a soluble B7-H1 or a soluble functional fragment of B7-H1; a soluble receptor for B7-H1 or a soluble functional fragment thereof; an antibody, or an antibody fragment, that binds to a receptor for B7-H1, e.g., the PD-1 receptor. The PD-1 receptor is described in greater detail in U.S. Pat. No. 6,808,710, the disclosure of which is incorporated herein by reference in its entirety.

In one embodiment, the agent itself is administered to a subject. Generally, the agent will be suspended in a pharmaceutically-acceptable carrier (e.g., physiological saline) and administered orally or by intravenous (i.v.) infusion, or injected subcutaneously, intramuscularly, intrathecally, intraperitoneally, intrarectally, intravaginally, intranasally, intragastrically, intratracheally, or intrapulmonarily. The agent can, for example, be delivered directly to a site of an immune response. e.g., a lymph node in the region of an affected tissue or organ or spleen. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100.0 mg/kg. Wide variations in the needed dosage are to be expected in view of the variety of compounds available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the compound in a suitable delivery vehicle (e.g., polymeric microparticles or implantable devices) may increase the efficiency of delivery, particularly for oral delivery.

Alternatively, where the agent is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in, or close to, lymphoid tissue draining an affected tissue or organ. Expression of the coding sequence can be directed, for example, to cells comprising the cancer tissue (e.g., tumor-infiltrating leukocytes and tumor cells) or immune-related cells, e.g., B cells, macrophages/monocytes, or interdigitating dendritic cells. This can be achieved by, for example, the use of polymeric, biodegradable microparticle or microcapsule delivery devices known in the art and/or tissue or cell-specific antibodies.

Another way to achieve uptake of the nucleic acid is using liposomes, which can be prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated subject. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

In addition, the method can be an ex vivo procedure that involves providing a recombinant cell which is, or is a progeny of a cell, obtained from a subject and has been transfected or transformed ex vivo with one or more nucleic acids encoding one or more agents that interfere with an interaction between B7-H1 and a receptor for B7-H1, so that the cell expresses the agent(s); and administering the cell to the subject. The cells can be cells obtained from a cancer tissue (e.g., tumor cells and/or tumor-infiltrating leukocytes) or from a non-cancerous tissue obtained preferably from a subject to whom these cells are to be administered or from another subject. The donor and recipient of the cells can have identical major histocompatibility complex (MHC; HLA in humans) haplotypes. Optimally, the donor and recipient are homozygotic twins or are the same individual (i.e., are autologous). The recombinant cells can also be administered to recipients that have no, or only one, two, three, or four MHC molecules in common with the recombinant cells, e.g., in situations where the recipient is severely immunocompromised, where only mismatched cells are available, and/or where only short term survival of the recombinant cells is required or desirable.

The efficacy of the agent can be evaluated both in vitro and in vivo. Briefly, the agent can be tested for its ability, for example, to (a) inhibit the interaction between B7-H1 and a receptor for B7-H1, (b) inhibit growth of cancer cells, (c) induce death of cancer cells, or (d) render the cancer cells more susceptible to cell-mediated immune responses generated by leukocytes (e.g., lymphocytes and/or macrophages). For in vivo studies, the agent can, for example, be injected into an animal (e.g., a mouse cancer model) and its effects on cancer are then assessed. Based on the results, an appropriate dosage range and administration route can be determined.

As used throughout the present application, the term "antibody" refers to a whole antibody (e.g., IgM, IgG, IgA, IgD, or IgE) molecule that is generated by any one of a variety of methods that are known in the art. The antibody can be a polyclonal or a monoclonal antibody. Also useful for the invention are chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 Current Protocols In Immunology, Coligan et al., ed. 2.8, 2.10 (Wiley Interscience, 1991). scFv fragments can be produced, for example, as described in U.S. Pat. No. 4,642,334, which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60.

As used herein, a "functional fragment" of a B7-H1 receptor means a fragment of a receptor for B7-H1 that is smaller than the wild-type mature B7-H1 receptor and has at least 10% (e.g., at least 10%, at least 20%, at least 30%, at least 40%, at least 50%, at least 60%, at least 70%, at least 80%, at least 90%, at least 95%, at least 98%, at least 99%, or 100% or more) of the ability of the wild-type mature receptor for B7-H1 to bind to B7-H1. As used herein, a "functional fragment" of B7-H1 means a fragment of the wild-type mature B7-H1 polypeptide that is smaller than the wild-type mature B7-H1 polypeptide and has at least 10% (e.g., at least 10%, at least 20%, at least 30%, at least 40%, at least 50%, at least 60%, at least 70%, at least 80%, at least 90%, at least 95%, at least 98%, at least 99%, or 100% or more) of the ability of the wild-type mature B7-H1 to bind to the B7-H1 receptor. Methods of testing and comparing the ability of molecules to bind to each other are known to those in the art.

As used herein, the term "soluble" distinguishes the receptors used in the present invention from their cell membrane-bound counterparts. A soluble receptor, or a soluble functional fragment of a receptor can contain, for example, an extracellular (ligand binding) domain, but lack the transmembrane region that causes retention of a receptor on the cell surface. Methods of producing soluble receptors or fragments thereof are known in the art and include, for example, expressing a DNA fragment encoding an extracellular domain of a receptor in a suitable host cell/expression vector system.

The term "treatment", as used herein, means administration of an agent to a subject, who has cancer (or is suspected of having cancer), with the purpose to cure, alleviate, relieve, remedy, prevent, or ameliorate the disorder, the symptom of the disorder, the disease state secondary to the disorder, or the predisposition toward the disorder. An "effective amount" of a therapeutic agent (or composition) is an amount of the agent (or composition) that is capable of producing a medically desirable result in a treated subject. The method of the invention can be performed alone or in conjunction with other drugs or therapy.

As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

Methods of Inhibiting Expression of B7-H1

Another aspect of the invention is a method of inhibiting the expression of B7-H1 in a tumor cell or a tumor-infiltrating leukocyte. The method involves: (a) identifying a subject with cancer, the cancer containing a target cell that expresses B7-H1, the target cell being a tumor cell or a tumor-infiltrating leukocyte; and (b) introducing into the target cell: (i) an antisense oligonucleotide that hybridizes to a B7-H1 transcript, the antisense oligonucleotide inhibiting the expression of B7-H1 in the cell; or (ii) a B7-H1 interference RNA (RNAi). These methods can be performed subsequent to, or without, performing any of the above-described methods.

Since, as noted above, aberrant B7-H1 expression impairs the function and survival of tumor-specific T cells, it is likely that by inhibiting the cellular expression of B7-H 1, as well as by interfering with the interaction between B7-H1 and its receptor, the anti-tumor immune responses can be restored. Thus, the method can be useful for therapy and/or prophylaxis of any cancer recited herein. The method can be used, for example, in the treatment of RCC.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with an antisense compound is chosen. Thus, for example, for modulation of polyadenylation, a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the internucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

Where antisense oligonucleotides per se are administered, they can be suspended in a pharmaceutically-acceptable carrier (e.g., physiological saline) and administered under the same conditions described above for agents that interfere with an interaction between B7-H1 and a receptor for B7-H1.

Where an expression vector containing a nucleic sequence (operably linked to a TRE) encoding the antisense oligonucleotide is administered to a subject, expression of the coding sequence can be directed to a tumor cell of tumor-infiltrating leukocyte in the body of the subject using any of the cell- or tissue-targeting techniques described above for vectors that express polypeptides that interfere with an interaction between B7-H1 and a receptor for B7-H1.

Double-stranded interfering RNA (RNAi) homologous to B7-H1 DNA can also be used to reduce expression of B7-H1 in tumor cells and/or tumor-infiltrating leukocytes. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of RNAi can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target B7-H1 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to tumor cells and/or tumor-infiltrating leukocytes.

Double-stranded RNAi interference can also be achieved by introducing into tumor cells and/or tumor-infiltrating leukocytes a polynucleotide from which sense and anti-sense RNAs can be transcribed under the direction of separate promoters, or a single RNA molecule containing both sense and anti-sense sequences can be transcribed under the direction of a single promoter.

It will be understood that certain drugs and small molecules can also be used inhibit expression of B7-H1 in tumor cells and/or tumor-infiltrating leukocytes.

One of skill in the art will appreciate that RNAi, drug, and small molecule methods can be, as for the antisense methods described above, in vitro and in vivo. Moreover, methods and conditions of delivery are the same as those for antisense oligonucleotides.

In any of the above methods of inhibiting the interaction between B7-H1 and a receptor for B7-H1 and of inhibiting expression of B7-H1, one or more agents (e.g., two, three, four, five, six, seven, eight, nine, ten, 11, 12, 15, 18, 20, 25, 30, 40, 50, 60, 70, 80, 100, or more) including, for example, inhibitory compounds, antisense oligonucleotides, RNAi, drugs, or small molecules (or vectors encoding them), can be used.

Moreover, such agents can be used together with one or more (e.g., two, three, four, five, six, seven, eight, nine, ten, 11, 12, 15, 18, 20, 25, 30, 40, 50, 60, 70, 80, 100, or more) supplementary agents, including immunomodulatory cytokines, growth factors, antiangiogenic factors, immunogenic stimuli, and/or antibodies specific for any of these. Such supplementary agents can administered before, simultaneous with, or after delivery of any of the above-listed agents.

Examples of immunomodulatory cytokines, growth factors, and antiangiogenic factors include, without limitation, interleukin (IL)-1 to 25 (e.g., IL-2, IL-12, or IL-15), interferon-γ (IFN-γ), interferon-α (IFN-α), interferon-β (IFN-β), tumor necrosis factor-α (TNF-α), granulocyte macrophage colony stimulating factor (GM-CSF), granulocyte macrophage colony stimulating factor (G-CSF), endostatin, angiostatin, and thrombospondin. Immunomodulatory cytokines, growth factors, antiangiogenic factors include substances that serve, for example, to inhibit infection (e.g., standard antimicrobial antibiotics), inhibit activation of T cells, or inhibit the consequences of T cell activation. For example, where it is desired to decrease a Th1-type immune response (e.g., in a DTH response), a cytokine such as interleukin (IL)-4, IL-10, or IL-13 or an antibody specific for a cytokine such as IL-12 or interferon-γ (IFN-γ) can be used. Alternatively, where it is desired to inhibit a Th2-type immune response (e.g., in an immediate type hypersensitivity response), a cytokine such as IL-12 or IFN-γ or an antibody specific for IL-4, IL-10, or IL-13 can be used as a supplementary agent. Also of interest are antibodies (or any of the above-described antibody fragments or derivatives) specific for proinflammatory cytokines and chemokines such as IL-1, IL-6, IL-8, tumor necrosis factor-α (TNF-α), macrophage inflammatory protein (MIP)-1, MIP-3α, monocyte chemoattractant protein-1 (MCP-1), epithelial neutrophil activating peptide-78 (ENA-78), interferon-γ-inducible protein-10 (IP10), Rantes, and any other appropriate cytokine or chemokine recited herein.

In some instances, it may be desired to increase the immune response in a subject by the administration of one or more immune response modifying-agents. Such immune response-modifying agents include, in addition to any of the immunomodulatory cytokines, growth factors, and angiogenic factors listed above, immunogenic stimuli that can be delivered via the antigen-specific T cell receptor (TCR) expressed on the surface of the T cell. More commonly, but not necessarily, such a stimulus is provided in the form of an antigen for which the TCR is specific. While such antigens will generally be protein, they can also be carbohydrates, lipids, nucleic acids or hybrid molecules having components of two or more of these molecule types, e.g., glycoproteins or lipoproteins. However, the immunogenic stimulus can also be provided by other agonistic TCR ligands such as antibodies specific for TCR components (e.g., TCR α-chain or β-chain variable regions) or antibodies specific for the TCR-associated CD3 complex. Antigens useful as immunogenic stimuli include alloantigens (e.g., a MHC alloantigen) on, for example, an antigen presenting cell (APC) (e.g., a dendritic cell (DC), a macrophage, a monocyte, or a B cell). DC of interest are interdigitating DC and not follicular DC; follicular DC present antigen to B cells. For convenience, interdigitating DC are referred to herein as DC. Methods of isolating DC from tissues such as blood, bone marrow, spleen, or lymph node are known in the art, as are methods of generating them in vitro from precursor cells in such tissues.

Also useful as immunogenic stimuli are polypeptide antigens and peptide-epitopes derived from them (see below). Unprocessed polypeptides are processed by APC into peptide-epitopes that are presented to responsive T cells in the form of molecular complexes with MHC molecules on the surface of the APC. Useful immunogenic stimuli also include a source of antigen such as a lysate of either tumor cells or cells infected with an infectious microorganism of interest. APC (e.g., DC) pre-exposed (e.g., by coculturing) to antigenic polypeptides, peptide-epitopes of such polypeptides or lysates of tumor (or infected cells) can also be used as immunogenic stimuli. Such APC can also be "primed" with antigen by culture with a cancer cell or infected cell of interest; the cancer or infected cells can optionally be irradiated or heated (e.g., boiled) prior to the priming culture. In addition, APC (especially DC) can be "primed" with either total RNA, mRNA, or isolated TAA-encoding RNA.

Alternatively, an immunogenic stimulus be provided in the form of cells (e.g., tumor cells or infected cells producing the antigen of interest). In addition, immunogenic stimuli can be provided in the form of cell hybrids formed by fusing APC (e.g., DC) with tumor cells [Gong et al. (2000) Proc. Natl. Acad. Sci. USA 97(6):2716-2718; Gong et al. (1997) Nature Medicine 3(5):558-561; Gong et al. (2000) J. Immunol. 165 (3):1705-1711] or infected cells of interest.

Also useful as immunogenic stimuli are heat shock proteins bound to antigenic peptide-epitopes derived from antigens (e.g., tumor-associated antigens or antigens produced by infectious microorganisms) [Srivastava (2000) Nature Immunology 1(5):363-366]. Heat shock proteins of interest include, without limitation, glycoprotein 96 (gp96), heat shock protein (hsp) 90, hsp70, hsp110, glucose-regulated protein 170 (grp170) and calreticulin. Immunogenic stimuli can include one or more (e.g., one, two, three, four, five, six, seven, eight, nine, ten, more) heat shock proteins isolated from tumor cells. Such tumor are preferably, but not necessarily, from the same subject (i) to whom the agent that interferes with the interaction between B7-H1 and a receptor for B7-H1 is to be delivered or (ii) in whose tumor cells or tumor infiltrating leukocytes the expression of B7-H1 is to be inhibited. The tumor cells can also be obtained, for example, from another individual having the same as the subject, or a related tumor-type. Alternatively, the heat shock protein can be isolated from mammalian cells expressing a transcriptosome prepared from tumor cells of interest.

As indicated above, immunogenic stimuli useful in the invention can be any of a wide variety of tumor cells, APC "primed" with tumor cells, hybrid cells, or TAA (see above), peptide-epitopes of such TAA, and APC "primed" with TAA or peptide-epitopes of them. As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a TAA can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Relevant TAA include, without limitation, any of the TAAs listed above.

Administrations of the agents and/or the one or more supplementary agents can be systemic (e.g., intravenous) or local, e.g., during surgery by direct injection or infusion into the tissue that comprises the cells of the cancer and/or tumor-infiltrating leukocytes. The administrations can also be by any of routes, doses, and schedules recited herein.

In addition, it is understood that the above-described methods can be used in combination with any one of a variety of other therapeutic modalities known in the art, such as, without limitation, chemotherapy, immunotherapy, radiotherapy, or gene therapy.

In both of the methods of inhibiting the interaction between B7-H1 and a receptor for B7-H1 and the methods of inhibiting expression of B7-H1, the cancer can be any cancer recited herein and includes, e.g., renal cell carcinoma. Subjects can be mammals and include, for example, humans, non-human primates (e.g., monkeys, baboons, or chimpanzees), horses, cows (or oxen or bulls), pigs, sheep, goats, cats, rabbits, guinea pigs, hamsters, rats, gerbils, or mice.

The following examples are meant to illustrate, not limit, the invention.

EXAMPLES

Example 1

Materials and Methods

Patient Selection

Upon approval from the Mayo Clinic Institutional Review Board, 429 patients were identified from Mayo Clinic Nephrectomy Registry that were previously treated with radical nephrectomy or nephron-sparing surgery for unilateral, sporadic clear cell RCC between 2000 and 2002. Since pathologic features and patient outcome differ by RCC subtype, all analyses were restricted to patients treated with clear cell RCC only, the most common of the RCC subtypes [Cheville et al. (2003) Am. J. Surg. Pathol. 27:612-624]. Since the hB7-H1-specific monoclonal antibody, 5H1 (see below), can reproducibly stain fresh-frozen, but not paraffin-fixed, tissue [Dong et al. (2002) Nature Med. 8:793-800], patients were selected based on availability of fresh-frozen tissue.

Pathologic Features

The pathologic features examined included histologic subtype, tumor size, primary tumor stage, regional lymph node involvement, and distant metastases at nephrectomy (2002 TNM), nuclear grade, and histologic tumor necrosis. The microscopic slides from all specimens were reviewed by a urologic pathologist without prior knowledge of patient outcome. Histologic subtype was classified according to the Union Internationale Contre le Cancer, American Joint Committee on Cancer, and Heidelberg guidelines [Storkel et al. (1997) Cancer 80:987-989; Kovacs et al. (1997) J. Pathol. 183:131-133]. Nuclear grade was assigned using standardized criteria [Lohse et al. (2002) Am. J. Clin. Pathol. 118:877-886]. Histologic tumor necrosis was defined as the presence of any microscopic coagulative tumor necrosis. Degenerative changes such as hyalinization, hemorrhage, and fibrosis were not considered necrosis.

Immunohistochemical Staining of Tumor Specimens

Cryosections generated from RCC tumors and normal renal cortical specimens (5 μm thickness) were mounted on Superfrost Plus slides, air dried, and fixed in ice-cold acetone. Sections were stained using the Dako Autostainer and Dako Cytomation Labeled Polymer (EnVision+) HRP detection Kit™ (Dako; Carpinteria, Calif.). Slides were blocked with $H_2O_2$ for 10 minutes followed by incubation with the primary anti-B7-H1 antibody for 30 minutes at room temperature. A horseradish peroxidase-conjugated secondary reagent (goat anti-mouse immunoglobulin) was then applied to the slides at room temperature for 15 minutes followed by incubation with chromogen-substrate for 10 minutes. Finally, sections were counter-stained for 3 minutes with modified Schmidt's Hematoxylin. The primary antibody used in this study was 5H1, a mouse anti-hB7-H1 monoclonal antibody [Dong et al. (2002) Nature Med. 8:793-800). Benign renal tumors and peripheral T cells were not stained in this study. Positive tissues controls for hB7-H1 staining were human tonsillar tissues. Irrelevant isotype-matched antibodies were used to control for non-specific staining.

Quantification of hB7-H1 Expression

The percentages of tumor cells and leukocytes that stained positive for hB7-H1 were quantified in 5-10% increments by a urologic pathologist without prior knowledge of patient outcome. The extent of leukocytic infiltration was assessed and recorded as absent, focal (scattered lymphoid aggregates), moderate, or marked. An adjusted score representing leukocytic hB7-H1 expression was calculated as the percentage of leukocytes that stained positive for hB7-H1 multiplied by the extent of leukocytic infiltration (0=absent, 1=focal, 2=moderate, 3=marked).

Statistical Methods

Comparisons between the pathologic features and hB7-H1 expression were evaluated using chi-square, Fisher's exact and Wilcoxon rank sum tests. Cancer-specific survival was estimated using the Kaplan-Meier method. The duration of follow-up was calculated from the date of nephrectomy to the date of death or last follow-up. Cause of death was determined from the death certificate or physician correspondence. Scatter plots of the percentage of cells that stained positive for hB7-H1 versus the difference in observed survival and the survival expected from a Cox proportional hazards regression model (formally known as a Martingale residual) were used to identify potential cut-off points for hB7-H1 expression [Therneau et al. (2000) Modeling Survival Data: Extending the Cox Model, ed. 1 (Springer-Verlag, Ann Arbor), pp. 87-92]. The associations of these cut points with death from RCC were evaluated using Cox proportional hazards regression models univariately and after adjusting for primary tumor stage, regional lymph node involvement, distant metastases, tumor size, nuclear grade, and histologic tumor necrosis, one feature at a time. The association of hB7-H1 expression with death from RCC was also adjusted for the Mayo Clinic SSIGN (Stage, Size, Grade, and Necrosis) Score, a prognostic composite score specifically developed for patients with clear cell RCC [Frank et al. (2002) J. Urol. 168:2395-2400]. Statistical analyses were performed using the SAS software package (SAS Institute, Cary, N.C.) and p-values <0.05 were considered statistically significant.

Example 2

Survival of RCC Patients with Fresh-Frozen Tissue Samples Available

Of the 429 patients eligible for the study, 196 (46%) had fresh-frozen tissue available for laboratory investigation. Patients with fresh-frozen tissues had larger tumors compared with those who did not (median tumor size 6.0 cm versus 5.0 cm; p=0.008). However, no other feature studied was significantly different between the two groups. Furthermore, there was not a statistically significant difference in cancer-specific survival between patients with and without fresh-frozen tissues (p=0.314).

At last follow-up, 39 of the 196 patients studied had died, including 30 patients who died from clear cell RCC at a median of 1.1 years following nephrectomy (range 0-2.5). Among the 157 patients who were still alive at last follow-up, the median duration of follow-up was 2.0 years (range 0-4.1). The estimated cancer-specific survival rates (standard error, number still at risk) at 1, 2, and 3 years following nephrectomy were 91.4% (2.1%, 148), 81.8% (3.3%, 78), and 77.9% (3.8%, 30), respectively.

Example 3

Correlation of hB7-H1 Expression in RCC Tumor Cells with Patient Outcome

Figure 1:
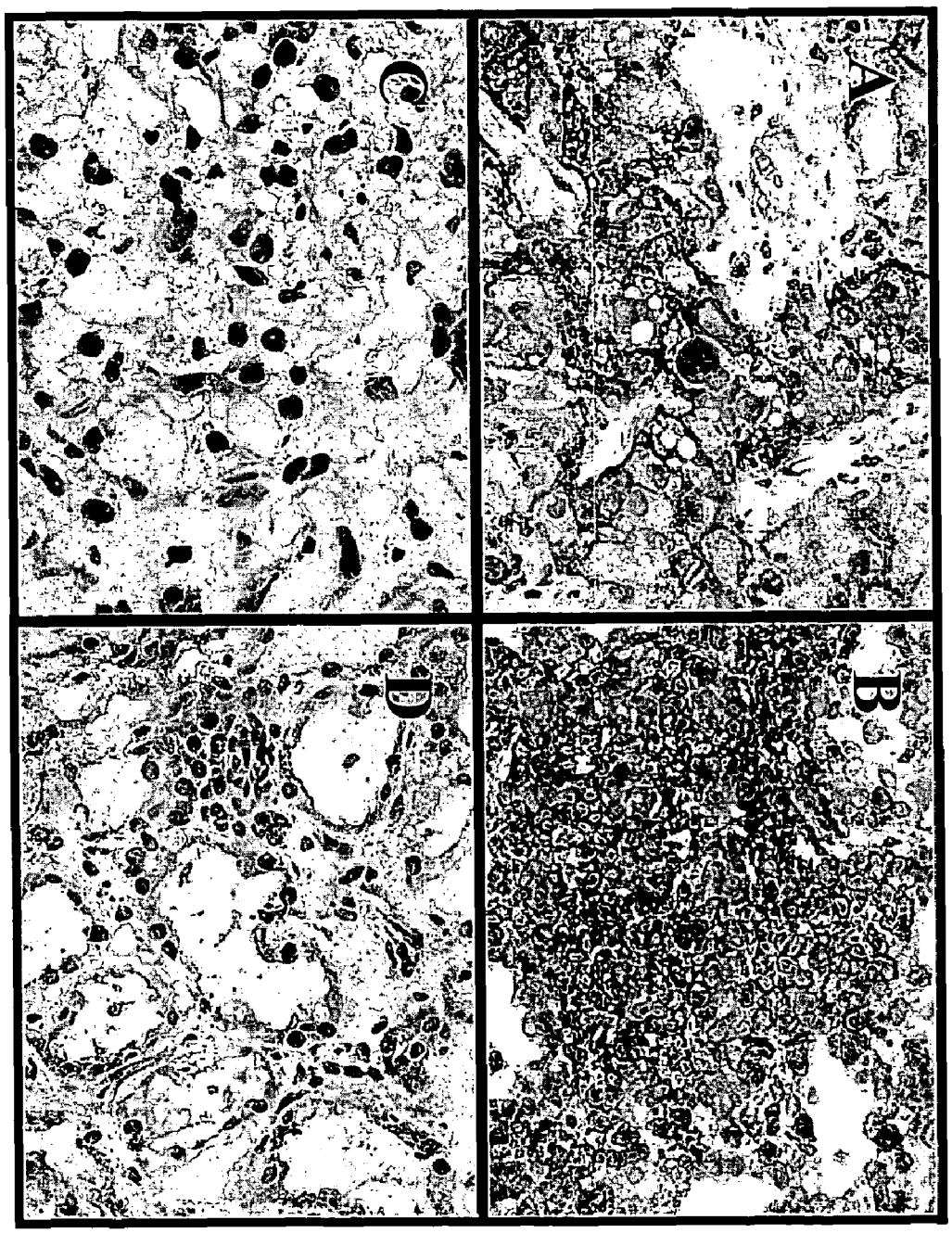
FIG. 1 is a series of photomicrographs (at a magnification of 400×) showing immunostaining (with an antibody specific for hB7-H1) of: an RCC specimen with high tumor cell hB7-H1 expression (FIG. 1A); an RCC specimen with high leukocyte hB7-H1 expression (FIG. 1B); an RCC specimen with no detectable hB7-H1 expression in either tumor cells or leukocytes (FIG. 1C); and a normal kidney specimen with no detectable hB7-H1 expression in the proximal tubules (FIG. 1D).

Immunohistochemical staining of the 196 clear cell RCC specimens revealed either no hB7-H1 expression by RCC tumor cells, or varying degrees of hB7-H1 expressed by either RCC tumor cells and/or RCC tumor-infiltrating leukocytes (Tables 1 and 2 and FIG. 1). In addition, proximal tubules within the renal cortex, from which RCC tumors are believed to arise, exhibited no hB7-H1 expression among the 20 normal renal cortical specimens studied (FIG. 1).

The percentages of tumor cells that stained positive for hB7-H1 for the 196 specimens studied are summarized in Table 1. A scatter plot of tumor hB7-H1 expression versus the expected risk of death for each patient suggested that a cut point of 10% would be appropriate for these data. There were 73 (37.2%) patients with specimens that had ≧10% tumor cell hB7-H1 expression.

TABLE 1

Percent Tumor hB7-H1 Expression in 196 Clear Cell RCC Specimens

| % hB7-H1 Expression | N (%) |
|---|---|
| 0 | 66 (33.7) |
| 5 | 57 (29.1) |
| 10 | 27 (13.8) |
| 15 | 4 (2.0) |
| 20 | 15 (7.7) |
| 25 | 3 (1.5) |
| 30 | 6 (3.1) |
| 40 | 2 (1.0) |

TABLE 1-continued

Percent Tumor hB7-H1 Expression in 196 Clear Cell RCC Specimens

| % hB7-H1 Expression | N (%) |
|---|---|
| 50 | 4 (2.0) |
| 60 | 3 (1.5) |
| 70 | 3 (1.5) |
| 80 | 2 (1.0) |
| 90 | 3 (1.5) |
| 100 | 1 (0.5) |

TABLE 2

Adjusted Score for Leukocyte hB7-H1 Expression in 196 Clear Cell RCC Specimens

| Leukocytic Infiltration* | % hB7-H1 Expression | Adjusted Score | N (%) |
|---|---|---|---|
| 0 | 0 | 0 | 81 (41.3) |
| 1 | 5 | 5 | 4 (2.0) |
| 1 | 10 | 10 | 1 (0.5) |
| 1 | 30 | 30 | 2 (1.0) |
| 1 | 50 | 50 | 4 (2.0) |
| 1 | 60 | 60 | 3 (1.5) |
| 1 | 70 | 70 | 22 (11.2) |
| 1 | 80 | 80 | 12 (6.1) |
| 1 | 90 | 90 | 10 (5.1) |
| 2 | 5 | 10 | 3 (1.5) |
| 2 | 10 | 20 | 4 (2.0) |
| 2 | 20 | 40 | 2 (1.0) |
| 2 | 30 | 60 | 2 (1.0) |
| 2 | 50 | 100 | 6 (3.1) |
| 2 | 60 | 120 | 1 (0.5) |
| 2 | 70 | 140 | 9 (4.6) |
| 2 | 80 | 160 | 7 (3.6) |
| 2 | 90 | 180 | 8 (4.1) |
| 3 | 5 | 15 | 1 (0.5) |
| 3 | 20 | 60 | 1 (0.5) |
| 3 | 30 | 90 | 4 (2.0) |
| 3 | 70 | 210 | 2 (1.0) |
| 3 | 80 | 240 | 4 (2.0) |
| 3 | 90 | 270 | 2 (1.0) |
| 3 | 100 | 300 | 1 (0.5) |

*The extent of leukocytic infiltration was recorded as 0 = absent, 1 = focally present, 2 = moderately present, or 3 = markedly present.

The associations of tumor hB7-H1 expression with death from RCC, both univariately and after adjusting for TNM stage, tumor size, nuclear grade, and histologic tumor necrosis are shown in Table 3. Univariately, patients with specimens that had ≧10% tumor hB7-H1 expression were close to 3 times more likely to die from RCC compared with patients with specimens that had <10% expression (risk ratio 2.91; 95% CI 1.39-6.13; p=0.005; FIG. 2A). In multivariate analyses, patients with specimens that had ≧10% tumor hB7-H1 expression were significantly more likely to die from RCC, even after adjusting for primary tumor stage, distant metastases, or primary tumor size.

TABLE 3

Associations of hB7-H1 Expression with Death from RCC in 196 Clear Cell RCC Specimens

| | Risk Ratio (95% CI)* | P-value |
|---|---|---|
| Tumor hB7-H1 Expression ≧10% | | |
| Univariate Model | 2.91 (1.39-6.13) | 0.005 |
| Adjusted for: | | |
| 2002 Primary Tumor Stage (T) | 2.83 (1.34-5.96) | 0.006 |

TABLE 3-continued

Associations of hB7-H1 Expression with Death
from RCC in 196 Clear Cell RCC Specimens

|  | Risk Ratio (95% CI)* | P-value |
|---|---|---|
| Regional Lymph Node Involvement (N) | 1.97 (0.87-4.45) | 0.103 |
| Distant Metastases (M) | 2.24 (1.06-4.73) | 0.035 |
| Primary Tumor Size | 2.88 (1.37-6.06) | 0.005 |
| Nuclear Grade | 1.96 (0.90-4.30) | 0.092 |
| Histologic Tumor Necrosis | 1.69 (0.78-3.65) | 0.183 |
| Leukocytic hB7-H1 Expression ≧100 | | |
| Univariate Model | 3.58 (1.74-7.37) | <0.001 |
| Adjusted for: | | |
| 2002 Primary Tumor Stage (T) | 3.34 (1.62-6.90) | 0.001 |
| Regional Lymph Node Involvement (N) | 3.59 (1.74-7.41) | <0.001 |
| Distant Metastases (M) | 2.16 (1.03-4.53) | 0.042 |
| Primary Tumor Size | 2.64 (1.27-5.46) | 0.009 |
| Nuclear Grade | 3.03 (1.46-6.29) | 0.003 |
| Histologic Tumor Necrosis | 2.87 (1.39-5.95) | 0.004 |
| High Aggregate Intratumoral hB7-H1 Expression | | |
| Univariate Model | 4.53 (1.94-10.56) | <0.001 |
| Adjusted for: | | |
| 2002 Primary Tumor Stage (T) | 4.07 (1.74-9.51) | 0.001 |
| Regional Lymph Node Involvement (N) | 3.36 (1.39-8.16) | 0.007 |
| Distant Metastases (M) | 3.12 (1.32-7.38) | 0.009 |
| Primary Tumor Size | 4.25 (1.82-9.91) | <0.001 |
| Nuclear Grade | 3.09 (1.28-7.50) | 0.012 |
| Histologic Tumor Necrosis | 2.68 (1.12-6.42) | 0.027 |

*Risk ratios represent the risk of death from clear cell RCC for the feature listed, either univariately or after multivariate adjustment. For example, patients with specimens that had ≧10% tumor hB7-H1 expression were 2.9 times more likely to die from RCC compared with patients with specimens that had <10% tumor hB7-H1 expression, even after adjusting for primary tumor size (p = 0.005).

The adjusted scores for leukocytic hB7-H1 expression are summarized in Table 2. There were 40 (20.4%) specimens with an adjusted leukocyte hB7-H1 score of 100 or greater (essentially moderate or marked leukocytic infiltration with at least 50% of the leukocytes staining positive for hB7-H1), which appeared to be a reasonable cut point to examine and illustrate the association of this feature with patient outcome. The associations of leukocyte hB7-H1 expression with death from RCC are summarized in Table 3. Univariately, patients with specimens that had an adjusted leukocyte hB7-H1 core ≧100 were 3.6 times more likely to die from RCC compared with patients that had specimens with scores <100 (risk ratio 3.58; 95% CI 1.74-7.37; p<0.001; FIG. 2B). Patients with specimens that demonstrated high levels of leukocyte hB7-H1 expression were significantly more likely to die from RCC even after adjusting for TNM stage, primary tumor size, nuclear grade, or histologic tumor necrosis.

Since both tumor and leukocyte hB7-H1 expression were significantly associated with patient outcome both univariately and after multivariate adjustment, the combination of these two features were evaluated. There were 87 (44.4%) specimens that had either ≧10% tumor hB7-H1 expression or an adjusted score for leukocyte hB7-H1 expression ≧100 (i.e., high aggregate intratumoral hB7-H1 expression). Twenty-six (13.3%) of these specimens had both features. Conversely, 109 (55.6%) specimens had <10% tumor hB7-H1 expression and <100 leukocyte hB7-H1 expression (i.e., low aggregate intratumoral hB7-H1 expression). The associations of this combined feature with death from RCC are summarized in Table 3. Univariately, patients with specimens that had high aggregate intratumoral hB7-H1 expression were 4.5 times more likely to die from RCC compared with patients with specimens that had both <10% tumor expression and <100 leukocyte expression (risk ratio 4.53; 95% CI 1.94-10.56; p<0.001). After adjusting for the Mayo Clinic SSIGN Score, patients with high aggregate intratumoral hB7-H1 expression remained over twice as likely to die from RCC compared with patients with low aggregate intratumoral hB7-H1, although this difference did not attain statistical significance (risk ratio 2.19; 95% CI 0.91-5.24; p=0.079). However, patients with specimens that had high aggregate intratumoral hB7-H1 expression were significantly more likely to die from RCC after adjusting for TNM stage, primary tumor size, nuclear grade, and histologic tumor necrosis, one feature at a time. The association of combined tumor and leukocyte hB7-H1 expression with the pathologic features under study were also investigated. High aggregate intratumoral hB7-H1 expression levels were significantly associated with regional lymph node involvement, distant metastases, advanced nuclear grade, and the presence of histologic tumor necrosis (Table 4).

TABLE 4

Associations of Tumor and Leukocyte hB7-H1 Expression with
Pathologic Features in 196 Clear Cell RCC Specimens

| | High Aggregate Intratumoral hB7-H1 Expression | | |
|---|---|---|---|
| | No | Yes | |
| | N = 109 | N = 87 | |
| Feature | N (%) | | P-value |
| 2002 Primary Tumor Stage | | | |
| pT1 and pT2 | 88 (80.7) | 62 (71.3) | 0.120 |
| pT3 and pT4 | 21 (19.3) | 25 (28.7) | |
| Regional Lymph Node Involvement | | | |
| pNx and pN0 | 108 (99.1) | 76 (87.4) | <0.001 |
| pN1 and pN2 | 1 (0.9) | 11 (12.6) | |
| Distant Metastases | | | |
| pM0 | 99 (90.8) | 69 (79.3) | 0.022 |
| pM1 | 10 (9.2) | 18 (20.7) | |
| Primary Tumor Size | | | |
| <5 cm | 46 (42.2) | 25 (28.7) | 0.051 |
| ≧5 cm | 63 (57.8) | 62 (71.3) | |
| Nuclear Grade | | | |
| 1 and 2 | 69 (63.3) | 23 (26.4) | <0.001 |
| 3 | 36 (33.0) | 50 (57.5) | |
| 4 | 4 (3.7) | 14 (16.1) | |
| Histologic Tumor Necrosis | | | |
| Absent | 94 (86.2) | 55 (63.2) | <0.001 |
| Present | 15 (13.8) | 32 (36.8) | |

A number of embodiments of the invention have been described. Nevertheless, it will be understood that various modifications may be made without departing from the spirit and scope of the invention. Accordingly, other embodiments are within the scope of the following claims.

What is claimed is:

1. A method for the treatment of a subject with cancer, wherein some or all cells of the cancer or some or all tumor-infiltrating leukocytes in cancer tissue express B7-H1, comprising administering to the subject an agent which is an antibody or an antigen-binding antibody fragment that interferes with an interaction between B7-H1 and a receptor for B7-H1, wherein said subject is a human or mouse and said B7-H1 is human B7-H1 (hB7-H1) or mouse B7-H1 (mB7-H1), respectively, wherein said subject has been identified for said administration by a test on a sample of cancerous tissue from said subject, wherein said tissue sample contains test cells, said test cells being cancer cells or tumor-infiltrating leukocytes, and said test was an assessment of the level of test cells in the tissue sample that express B7-H1, said identification being made if, the level of test cells in the tissue sample that express said B7-H1 is less than an immuno-inhibitory threshold level, wherein said immuno-inhibitory threshold level is determined by performing a statistical analysis of the correlation between the proportion of cells expressing B7-H1 in a group of subjects with said cancer and an expected risk of death in said group of subjects, and assigning a statistically significant cut-off value for said correlation.

2. The method of claim 1, wherein the subject is a human subject.

3. The method of claim 2, wherein the agent is an antibody or an antibody fragment that binds to said human B7-H1.

4. The method of claim 3, wherein the antibody or antibody fragment is administered before, simultaneous with, or after administration of one or more immunomodulatory cytokines, growth factors, or antiangiogenic factors.

5. The method of claim 4, wherein the immunomodulatory cytokine, growth factor, or antiangiogenic factor is at least one of: an interleukin, interferon-α (IFN-α), interferon-β (IFN-β), interferon-γ (IFN-γ), tumor necrosis factor-α (TNF-α), granulocyte macrophage colony stimulating factor (GM-CSF), granulocyte macrophage colony stimulating factor (G-CSF), endostatin, angiostatin, or thrombospondin.

6. The method of claim 3, wherein the cancer is renal cancer.

7. The method of claim 3, wherein the cancer is hematological cancer, neurological cancer, melanoma, breast cancer, lung cancer, head and neck cancer, gastrointestinal cancer, liver cancer, pancreatic cancer, genitourinary cancer, bone cancer, or vascular cancer.

8. The method of claim 3, wherein the antibody is a humanized antibody.

9. The method of claim 3, wherein the antibody is an IgG antibody.

10. The method of claim 3, wherein the antibody or antibody fragment is a monoclonal antibody or a fragment of a monoclonal antibody.

11. The method of claim 10, wherein the antibody or antibody fragment is produced using a recombinant DNA technique.

12. The method of claim 8, wherein the humanized antibody is made from a mouse antibody.

13. The method of claim 2
wherein, if the level of test cells expressing said B7-H1 is less than an immuno-inhibitory threshold level, the subject is more likely to benefit from immunotherapy than another subject with the same cancer but whose corresponding level of test cells expressing said B7-H1 is equal to, or greater, than the immuno-inhibitory threshold level.

14. The method according to claim 2 wherein said tumor-infiltrating leukocytes comprise T lymphocytes, B lymphocytes, bone marrow-lineage cells, granulocytes, monocytes, macrophages, dendritic cells, histiocytes, or natural killer cells.

15. The method according to claim 14, wherein T lymphocytes comprise CD8+ T lymphocytes and/or CD4+ T lymphocytes and said granulocytes comprise neutrophils, eosinophils, or basophils.

16. A method of identifying a subject having renal cell carcinoma (RCC) suitable for B7-H1 based immunotherapy, comprising
(i) providing a cancer tissue sample from a subject with RCC, wherein the tissue sample contains test cells, the test cells being cancer cells or tumor-infiltrating leukocytes; and
(ii) assessing the level of test cells in the tissue sample that express B7-H1,
wherein said subject is a human or mouse and said B7-H1 is human B7-H1 (hB7-H1) or mouse B7-H1 (mB7-H1), respectively;
wherein, if the level of test cells expressing said B7-H1 is less than an immuno-inhibitory threshold level, the subject is determined to benefit from immunotherapy with an agent which is an antibody or an antigen-binding antibody fragment that interferes with an interaction between B7-H1 and a receptor for B7-H1, wherein said immuno-inhibitory threshold level is determined by performing a statistical analysis of the correlation between the proportion of cells expressing B7-H1 in a group of subjects with RCC and an expected risk of death in said group of subjects, and assigning a statistically significant cut-off value for said correlation.

17. The method according to claim 16 wherein if the level of test cells expressing said B7-H1 is less than an immuno-inhibitory threshold level, the subject is determined to more likely benefit from said agent than another subject with the same cancer but whose corresponding level of test cells expressing said B7-H1 is equal to, or greater, than the immuno-inhibitory threshold level.

18. The method according to claim 1, wherein the cancer is hematological cancer or melanoma.

19. The method according to claim 1, wherein the the statistical analysis is performed using a scatter plot.

20. The method according to claim 16, wherein the immuno-inhibitory threshold level is determined by performing a scatter plot of the level of test cells expressing said B7-H1 in a subject with RCC versus an expected risk of death in said subject; correlating said level of test cells expressing said B7-H1 with said expected risk of death; and assigning a cut-off value which attains statistical significance for said correlation.

21. The method according to claim 20, wherein the immuno-inhibitory threshold level is 10% B7-H1 positive cells in a test cell population.

22. The method according to claim 19, wherein the immuno-inhibitory threshold level is 10% B7-H1 positive cells in a test cell population.

* * * * *